(12) United States Patent
Caruso et al.

(10) Patent No.: US 8,964,940 B2
(45) Date of Patent: Feb. 24, 2015

(54) DYNAMICALLY ADJUSTABLE FILAMENT CONTROL THROUGH FIRMWARE FOR MINIATURE X-RAY SOURCE

(71) Applicants: David J. Caruso, Groton, MA (US); Mark T. Dinsmore, Sudbury, MA (US)

(72) Inventors: David J. Caruso, Groton, MA (US); Mark T. Dinsmore, Sudbury, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 296 days.

(21) Appl. No.: 13/683,376

(22) Filed: Nov. 21, 2012

(65) Prior Publication Data

US 2014/0140474 A1 May 22, 2014

(51) Int. Cl.
H05G 1/32 (2006.01)
G01N 23/02 (2006.01)
H05G 1/30 (2006.01)
H05G 1/34 (2006.01)

(52) U.S. Cl.
CPC .............. H05G 1/32 (2013.01); G01N 23/02 (2013.01); H05G 1/34 (2013.01)
USPC ........... 378/110; 378/101; 378/104; 378/106; 378/108; 378/109; 378/111; 378/113

(58) Field of Classification Search
USPC ......... 378/101, 104, 106, 108, 109, 110, 111, 378/113
See application file for complete search history.

(56) References Cited

U.S. PATENT DOCUMENTS

| | | | | |
|---|---|---|---|---|
| 2,512,193 A | * | 6/1950 | Zavales | 315/102 |
| 3,348,051 A | * | 10/1967 | Weighart et al. | 378/102 |
| 3,916,251 A | * | 10/1975 | Hernandez et al. | 378/110 |
| 4,172,223 A | * | 10/1979 | Ishijima et al. | 378/108 |
| 4,322,625 A | * | 3/1982 | Daniels et al. | 378/110 |
| 4,775,992 A | | 10/1988 | Resnick et al. | |
| 4,930,146 A | * | 5/1990 | Flakas et al. | 378/110 |
| 7,406,154 B2 | * | 7/2008 | Resnick | 378/113 |
| 7,448,802 B2 | * | 11/2008 | Oettinger et al. | 378/203 |
| 2003/0021377 A1 | * | 1/2003 | Turner et al. | 378/102 |
| 2006/0115050 A1 | * | 6/2006 | Resnick | 378/108 |
| 2012/0082292 A1 | * | 4/2012 | Zou et al. | 378/16 |
| 2013/0315378 A1 | * | 11/2013 | Yabugami | 378/98 |
| 2014/0140474 A1 | * | 5/2014 | Caruso et al. | 378/53 |

FOREIGN PATENT DOCUMENTS

WO 2004079752 A2 9/2004

OTHER PUBLICATIONS

Jaisingh Rajwade, "Emission Control System for an X-Ray Tube," M.S.E.E. Thesis, Cleveland State University (2001), pp. 1-111.

* cited by examiner

*Primary Examiner* — David A Vanore
(74) *Attorney, Agent, or Firm* — Ion C. Abraham

(57) ABSTRACT

An x-ray beam control system includes a feedback control loop circuit having a modulation circuit. The feedback control loop circuit generates a control signal. A x-ray tube, has a filament response profile of tube current versus filament temperature that is non-linear. A compensation circuit receives the control signal and modifies the control signal according to a compensating function that is matched to the filament response profile. The modulation circuit receives the modified control signal and generates a drive signal. The x-ray tube receives the drive signal at a filament thereof, and outputs a tube current signal having a linear response to the control signal. The feedback control loop circuit receives the tube current signal.

28 Claims, 8 Drawing Sheets

DYNAMICALLY ADJUSTABLE FILAMENT CONTROL THROUGH FIRMWARE FOR MINIATURE X-RAY SOURCE

BACKGROUND

Miniature x-ray tubes have been used extensively in portable equipment for non-destructive analysis, material characterization, imaging and medical applications. The portability of the instrumentation and point of use nature of the resulting systems demands that they be able to make measurements rapidly and consistently under a range of operating parameters. One of the key aspects of this type of operation is the ability of the x-ray tube to begin generating stable output tube current as rapidly as possible.

To date, miniature x-ray tubes have utilized primarily analog circuitry to control the filament of the x-ray tube. The basic problem with the control system is that the transfer function gain increases dramatically as the requested tube current increases. The highest open loop gain occurs at the maximum allowable operating tube current for the x-ray tube. For stable operation using an analog control circuit, the overall gain needs to be set to ensure stability at this maximum gain. Optimization for maximum current gain allows for fast turn-on and settling time with minimum overshoot of the tube current when running at maximum tube current.

The issue with the analog circuit implementation is that when requesting lower tube currents, the gain is much lower than in maximum current operation resulting in excessive turn-on and settling times. These increases in turn-on and settling time can result in incorrect measurements or increased assay times for proper results.

SUMMARY

An x-ray beam control system includes a feedback control loop circuit having a modulation circuit. The feedback control loop circuit generates a control signal. A x-ray tube, has a filament response profile of tube current versus filament temperature that is non-linear. A compensation circuit receives the control signal and modifies the control signal according to a compensating function that is matched to the filament response profile. The modulation circuit receives the modified control signal and generates a drive signal. The x-ray tube receives the drive signal at a filament thereof, and outputs a tube current signal having a linear response to the control signal. The feedback control loop circuit receives the tube current signal.

DETAILED DESCRIPTION

Figure 1:
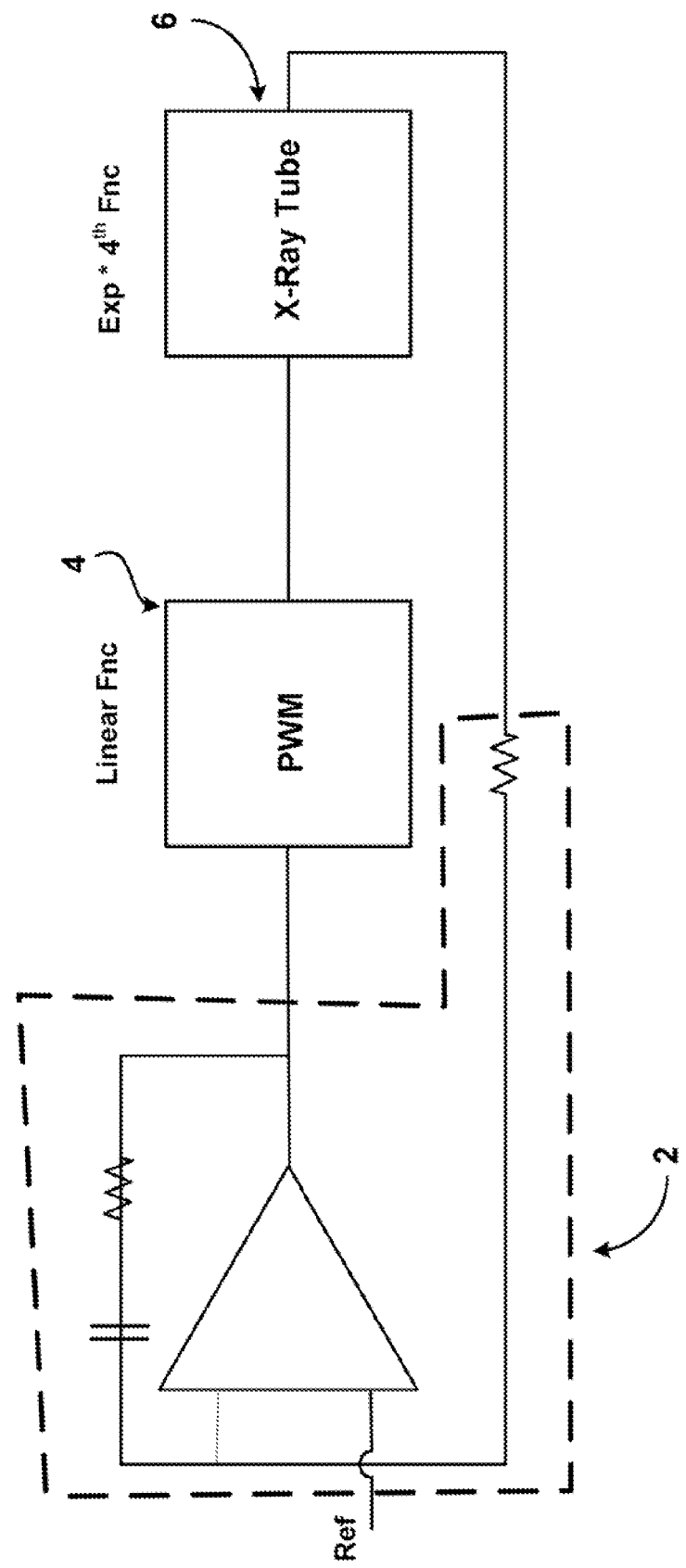
FIG. 1 is a basic schematic for the control of the tube current in a miniature x-ray tube of the prior art.

FIG. 1 is a functional block diagram corresponding to the control of the tube current in a miniature x-ray tube of the prior art. A control circuit 2 (shown within the dashed portion) provides an output to a pulse width modulation (PWM) circuit 4. The PWM circuit 4 generates a filament drive signal to an x-ray tube 6. The output of the x-ray tube 6 is an input to the control circuit 2.

Figure 2:
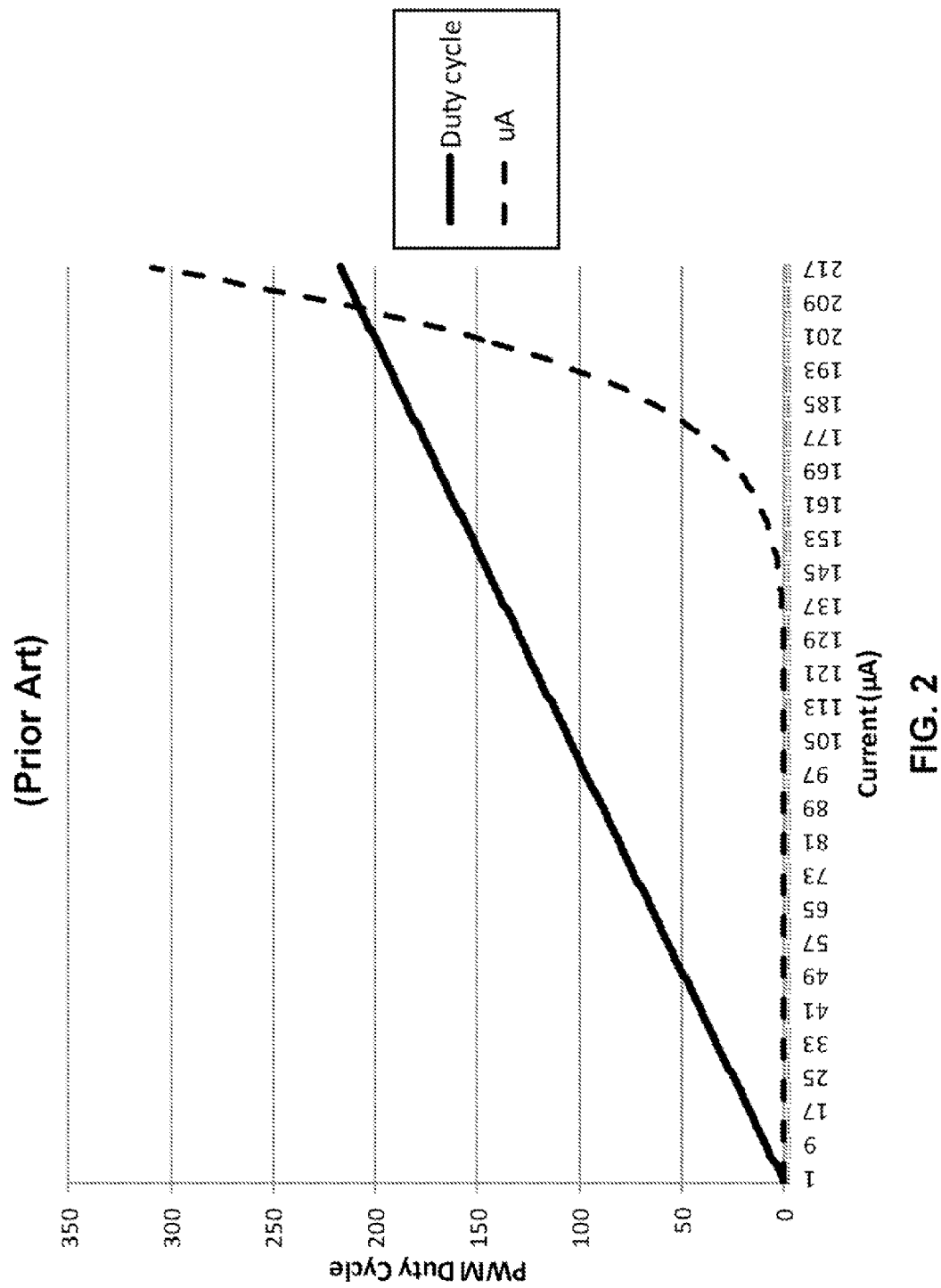
FIG. 2 is a graph of the tube current versus raw PWM duty cycle far x-ray tube control system of FIG. 1.

FIG. 2 is a graph of the tube current versus raw PWM voltage for a prior art x-ray control system. This is a typical graph of duty cycle vs. output of an x-ray tube. The tube current is a non-linear function of duty cycle. Because of the non-linear relationship, no current is generated for the majority of the PWM duty ratios. When a non-linear response is introduced into the control circuit, issues arise with the stability of the feedback loop, e.g. longer rise times, overshooting, and settling longer settling times. These result in slower turn-on time times for the x-ray tube.

Figure 3:
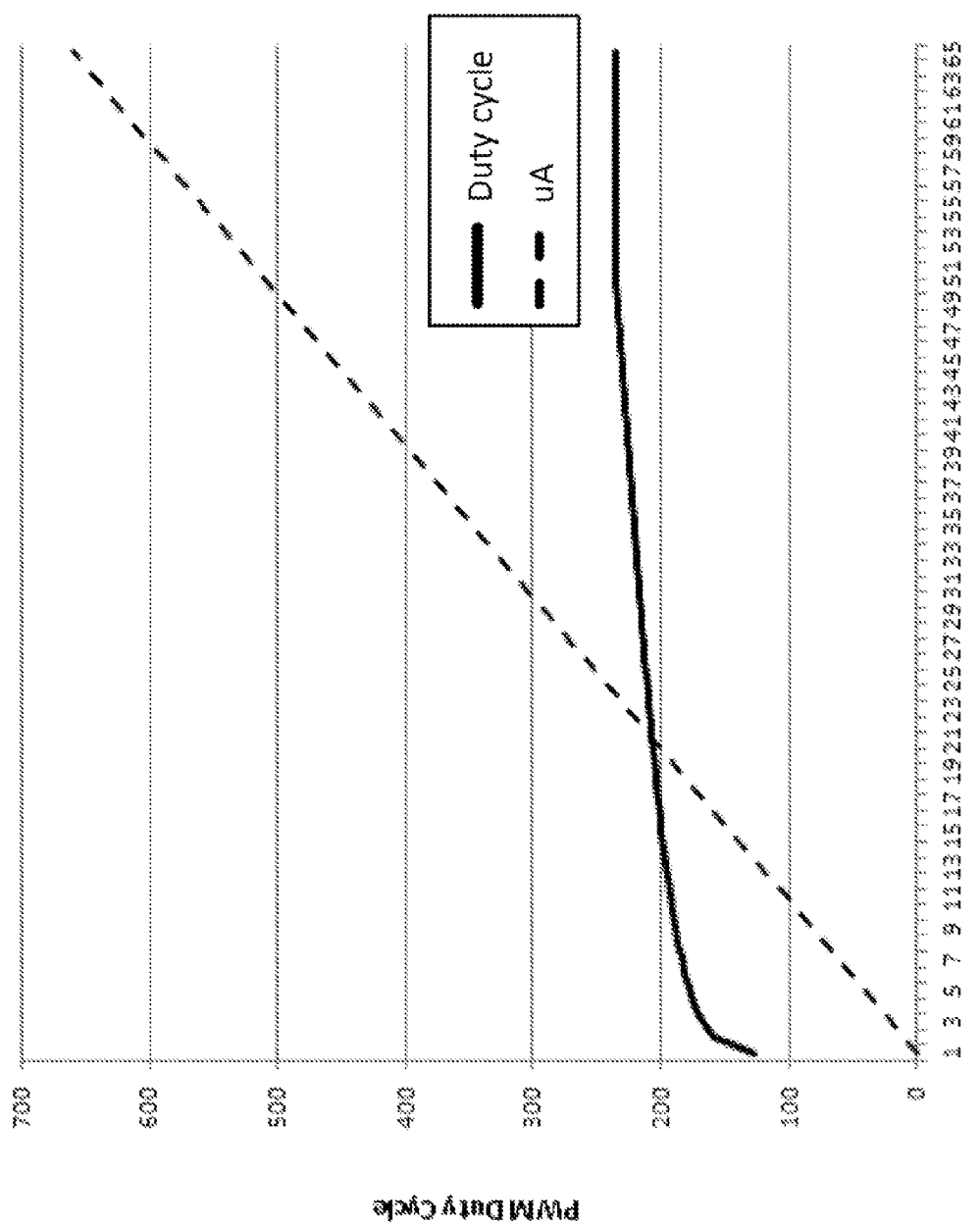
FIG. 3 is a graph of the drive PWM current versus the raw PWM duty cycle.

FIG. 3. is a graph of the drive PWM versus the raw PWM voltage. This is the linearization of the duty cycle vs. the output of the x-ray tube control system. In an embodiment of the invention as will be described further, the linear portion of the tube current is provided as an input to a control circuit. This improves the stability of the feedback loop by reducing times, minimizing overshooting, and shortening settling times.

With the processing power available in a firmware controlled system, a compensating function, can be generated that will linearize the response of the tube current of an x-ray beam to the filament drive signal.

As each x-ray tube has a unique filament response profile, the best way to generate an accurate compensating function, e.g. inverse transfer function, is to measure the response of the tube current in place and generate a unique curve for each device.

The filament drive signal is a modulated signal, e.g. a pulse width modulated square wave (PWM), that is applied to the filament which averages the drive pulse width modulation to produce a filament heating power. Because of the non-linear relationship, no current is generated for the majority of the PWM duty ratios. Ideally one would like a linear relationship between the PWM duty ratios and the tube current. For a predetermined PWM voltage, this can be accomplished by measuring the response of the tube current at each step of the modulated signal. An inverse transfer function is generated and stored. Alternatively, the values of the inverse transfer function may be stored as a lookup table. The lookup table values are applied to the control signal and become the filament drive signal. The response of the tube current of the x-ray tube is now a linear response when the filament drive signal is applied. A look up table may be generated for multiple PWM voltages.

This measurement may be performed at the time of manufacture of the x-ray tube or upon use and is stored on the device in non-volatile memory. During operation, the firmware uses this linearized table to control the tube current loop with constant turn-on and settling times regardless of requested current.

Additionally, this measurement can be re-run periodically to account for changes in the filament response profile of the x-ray tube. Comparing the tables over time can give indication to the relative health of the x-ray tube filament and used for predictive maintenance.

Each x-ray tube has a unique filament response profile of tube current versus filament temperature which is non-linear. The tube current is the stream of electrons between the cathode and the anode. The tube current is measured in milliamps and is controlled by regulating the low-voltage, heating current applied to the cathode. The higher the temperature of the filament, the larger the number of electrons that leave the cathode and travel to the anode. The milliamp or current setting of the controller regulates the filament temperature, which relates to the intensity of the X-ray output. The tube current at different filament current (as measured by the PWM duty cycle) is measured in place and a unique curve or transfer function for each device is generated. A compensating transfer function, e.g. inverse transfer function, matching the unique filament response profile is generated. This function is used to alter the filament drive signal so the resulting x-ray tube current is a linear response to the control signal.

Figure 4:
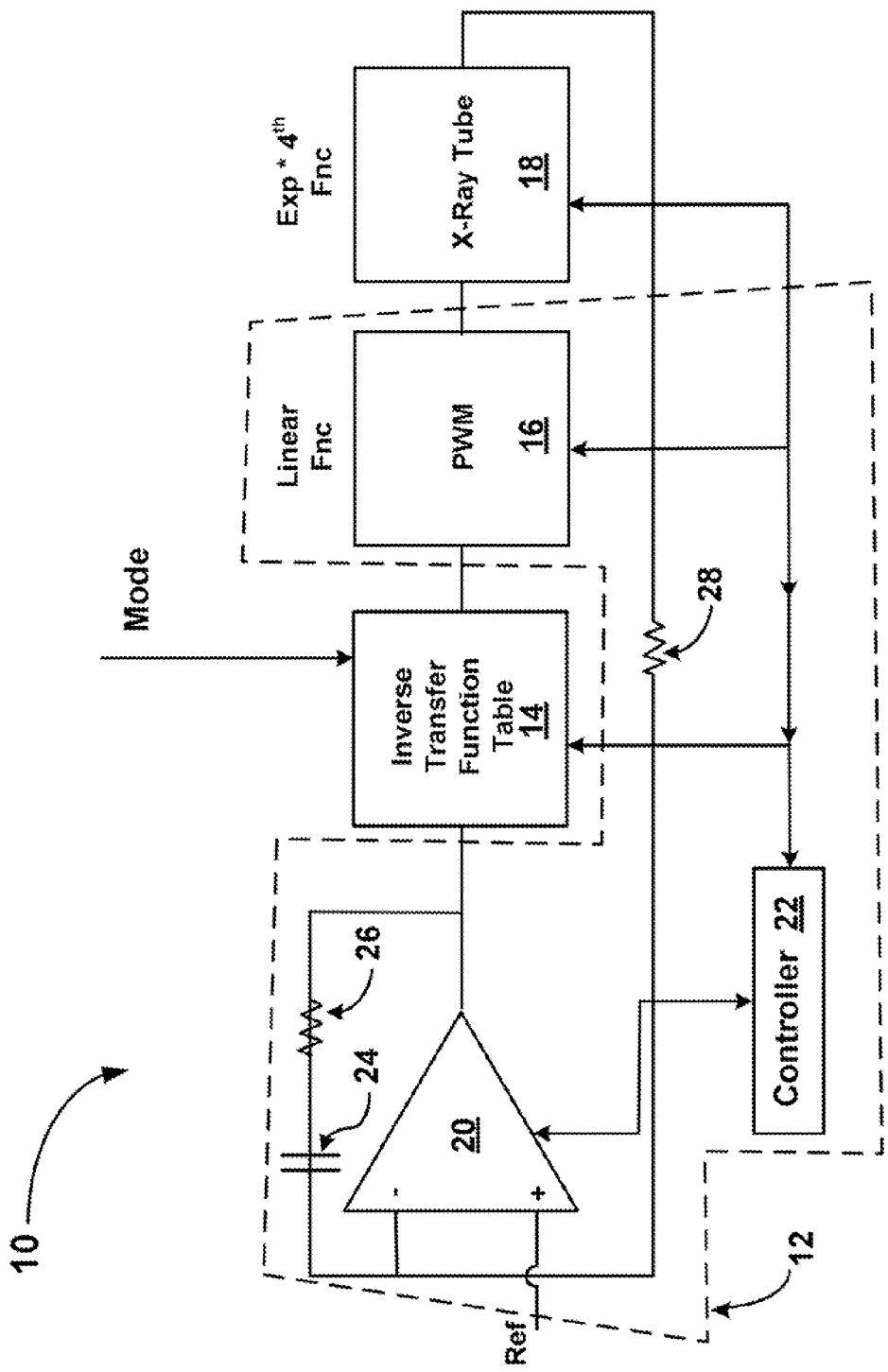
FIG. 4 is a basic schematic showing the inverse transfer function compensation for control of the miniature x-ray tube.

FIG. 4. illustrates a basic schematic diagram for a x-ray system 10 showing the inverse transfer function compensation for control of the miniature x-ray tube. A control feedback circuit 12 (shown within a dashed portion) receives the desired setting and generates a control signal. The compensation circuit 14 receives the control signal and mode setting and outputs a modified control signal indicative of the input signals. The modulation circuit 16, e.g. a pulse width modulation (PWM) circuit or an analog control signal, receives and applies the modified control signal as a filament drive signal to an x-ray tube 18. A feedback resistor 28 interposes the output of the x-ray tube 18 and the negative input of the amplifier 20.

The control feedback circuit is a closed loop control system. One suitable feedback control circuit 12 is a proportional integral derivative (PID) controller. A PID controller 12 calculates an "error" value as the difference between a measured process variable and a desired set point. The controller 12 attempts to minimize the error by adjusting the process control inputs.

The PID controller calculation involves three separate constant parameters, and is accordingly sometimes called three-term control: the proportional, the integral and derivative values, denoted P, I, and D. Heuristically, these values can be interpreted in terms of time: P depends on the present error, I on the accumulation of past errors, and D is a prediction of future errors, based on current rate of change. The weighted sum of these three actions is used to adjust the process via a control element such as the power supplied to the x-ray tube 18.

When the feedback control circuit 12 is a PID controller, it includes an amplifier 20 having a positive input and a negative input. The positive input receives the desired setting. A serially connected capacitor 24 and resistor 26 interpose the negative input and the output of the amplifier 20. The output of the amplifier 20 provides the control signal to the inverse transfer function table 14. Within the feedback control circuit 12, the modulation circuit receives the modified control signal from the compensation circuit 14 and applies it to the x-ray tube 18. Further, a controller 22 bi-directionally communicates with the amplifier 20, the compensation circuit 14, the modulation circuit 16, and the x-ray tube 18.

In one embodiment, the compensation circuit 14 may be an inverse transfer function table, e.g. memory having stored values of the compensating function. In another embodiment, the compensation circuit 14 includes a controller storing the compensating function, e.g. inverse transfer function. The control signal is then modified dynamically, e.g. real time, by the inverse transfer function.

In another embodiment, multiple inverse transfer functions and a mode setting may be selected depending on the operating conditions. These operating conditions can include but are not limited to high current filament, precision current mode filament, filament health, operating hours, humidity, ambient temperature, and desired PWM voltage.

To illustrate, the mode settings of high current filament and precision current mode filament to allow the use of particular portions of the inverse transfer function table for more precise control over a smaller range of current, or conversely less precision over a larger range of currents. One can envision having a high current filament mode for large ranges of operating current and precision current filament mode for just a portion of the operating range, but allowing for more precise initialization with the same number of table entries.

Figure 5A:
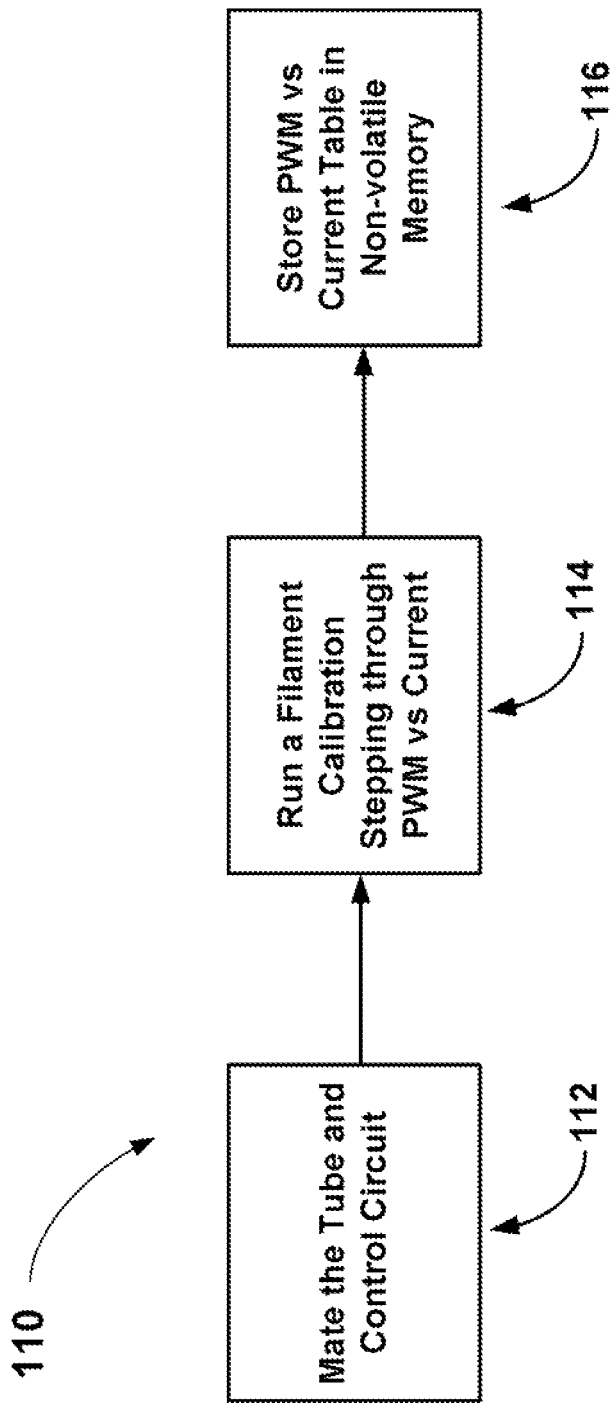
FIG. 5A shows a block diagram of the filament control system in manufacture, operation and maintenance wherein the tube and the control circuit are mated, filament calibration is run by to create a pulse width modulation (PWM) signal vs. current profile, and a compensating function is determined that corresponds to the filament calibration.
Figure 5B:
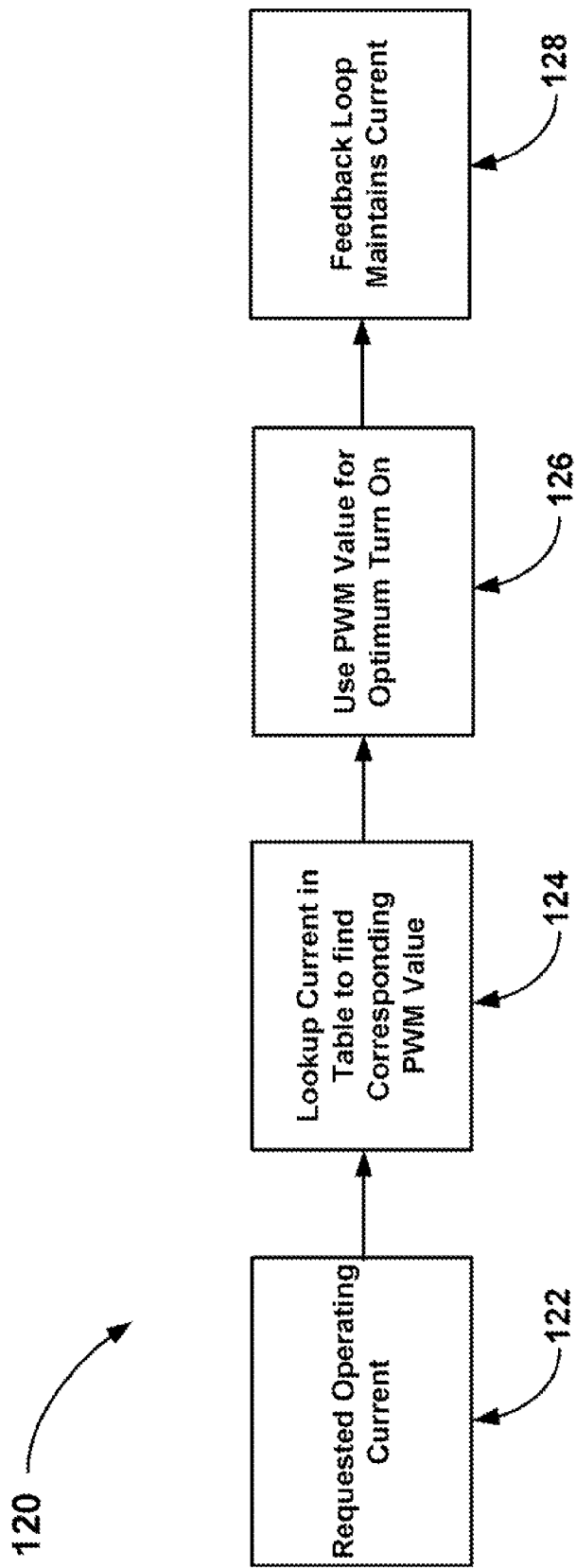
FIG. 5B shows a block diagram of the filament control system in manufacture, operation and maintenance wherein the operating current is requested, the current is looked up in the PWM signal vs. current table to find the corresponding PWM value, the corresponding PWM value is applied as the optimum turn on value, and a feedback loop maintains the current corresponding to the PWM value.
Figure 5C:
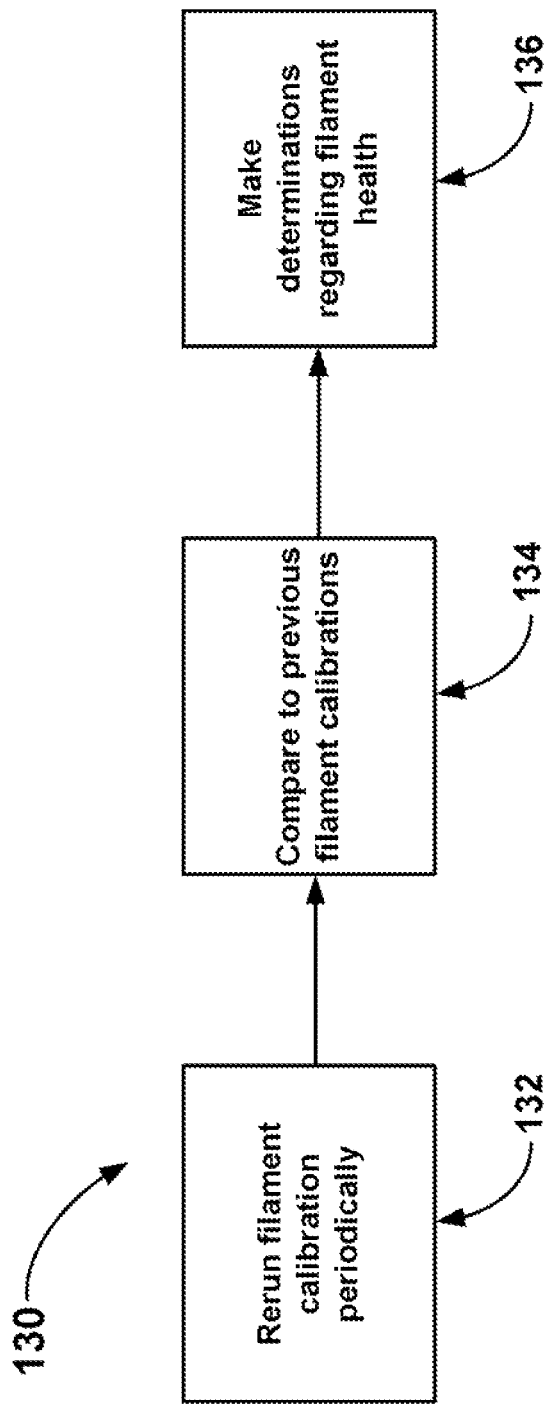
FIG. 5C shows a process flowchart corresponding to the filament control system during maintenance or monitoring, wherein the filament calibration process is run at the desired schedule, the generated profile is compared to the previous filament calibrations, and a determination is made regarding filament health.

FIG. 5A-5C are process flowcharts corresponding to the filament control system in manufacture, operation and maintenance.

FIG. 5A is a process flowchart 110 corresponding to the filament control system in manufacture. In step 112, the tube and the control circuit are mated. In step 114, filament calibration is run by to create a pulse width modulation (PWM) signal vs. current profile. To illustrate, this can be accomplished by measuring the response of the tube current at each step of the modulated signal. In step 116, a compensating function is determined that corresponds to the filament calibration. The compensating function is stored as a PWM vs. current table in non-volatile memory. When the compensating function is applied to the control signal, the output of the x-ray tube will have a linear response.

In operation, an x-ray tube output is a non-linear response since the emitted current from the thermionic emitter is an exponential function of temperature. The temperature is proportional to the $4^{th}$ power of the filament drive power. Compensating for this type of rapidly changing function is very difficult in the analog domain. Ideally, a linear response between the tube current and the filament drive signal could be established across the entire operating range of the x-ray tube. This would allow for similar turn-on and settling times with minimal overshoot across the entire operating range of tube currents.

In operation, as will be described in FIG. 6B, the control signal is deliberately distorted by the compensating transfer function means so that after it has been distorted again by the x-ray tube, the input to PID controller will be a linear signal.

FIG. 5B is a process flowchart 120 corresponding to the filament control system in operation. In step 122, the operating current is requested. In step 124, the current is looked up in the PWM signal vs. current table to find the corresponding PWM value. In step 126, the corresponding PWM value is applied as the optimum turn on value. In step 128, the feedback loop maintains the current corresponding to the PWM value.

FIG. 5C is a process flowchart 130 corresponding to the filament control system during maintenance or monitoring. In step 132, the filament calibration process is run at the desired schedule. In step 134, the generated profile is compared to the previous filament calibrations. In step 136, a determination is made regarding filament health.

In one embodiment, to illustrate, the controller acquires the first and the second profiles of the x-ray tube at different times as described above and may derive the. A comparator of the controller receives and compares the first filament response profile and the second filament response profile. The output of the comparator is a filament health indicator. The controller may acquire the first and the second filament response profile of the x-ray tube upon receiving a request from a user or at predetermined operating intervals.

While the aforementioned has been described with respect to filament temperature, any of the embodiments of the invention can be applied to alternatively to any non-linear parameter of the x-ray tube.

Figure 6:
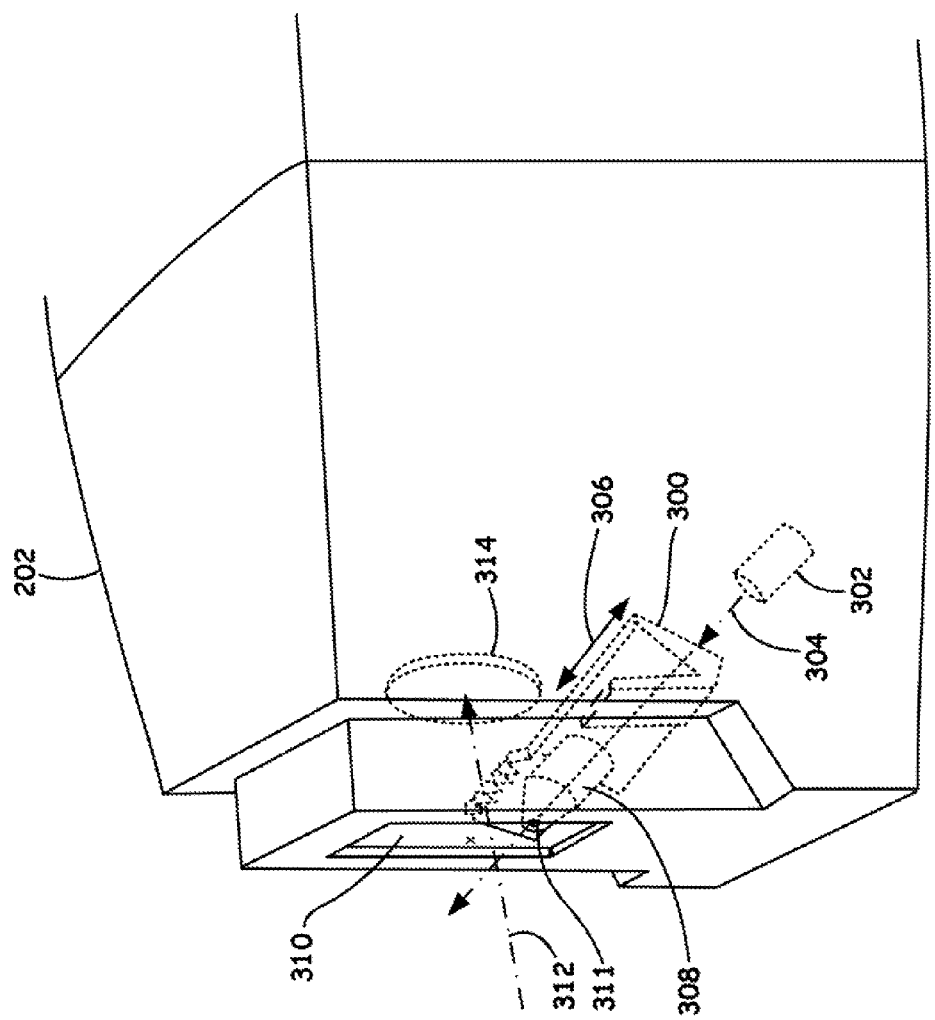
FIG. 6 shows an example close up view embodiment of a snout of a hand held analyzer with a collimated shutter.

FIG. 6 is a dose up view of a snout 202 of a hand held analyzer showing a collimated shutter 300. The collimated shutter 300 includes a tube 308. An x-ray tube 302 produces a x-ray beam 304 directed towards one side (the back) of the collimated shutter 300. As shown by an arrow 306, the collimated shutter 300 can move laterally or rotationally between at least two positions. In the position shown in FIG. 6, the tube 308 is aligned with the x-ray beam 304, between the x-ray tube 302 and a window 310, such that the x-ray beam may pass through the tube 308, exit the snout 202 via the window 310 and strike sample (not shown). The end of the tube 308 from with the primary x-rays exit defines a distal exit aperture 311. Fluorescent x-rays 312 from the sample enter the window 310 and strike a detector 314 (shown in phantom). The window 310 may be covered by a thin sheet of x-ray transparent material (not shown), such as a polyimide film, to prevent dirt or other contaminants from entering the snout 202 through the window 310. A suitable polyimide film is available under the tradename Kapton from I.I. du Pont de Nemours and Company.

We claim:

1. An x-ray beam control system comprising:
   a feedback control loop circuit, including a modulation circuit, generating a control signal;
   an x-ray tube, having a filament response profile of tube current versus filament temperature which is non-linear; and
   a compensation circuit receiving the control signal, modifying the control signal according to a compensating function that is matched to the filament response profile;
   wherein:
      the modulation circuit receives the modified control signal and generates a drive signal;
      the x-ray tube receives the drive signal at a filament thereof, and outputs a tube current signal having a linear response to the control signal; and
      the feedback control loop circuit receives the tube current signal.

2. The x-ray beam control system as in claim 1 wherein the feedback control loop circuit is a PID control loop circuit.

3. The x-ray beam control system as in claim 1, wherein the modulation circuit is a pulse width modulation circuit.

4. The x-ray beam control system, as in claim 1, wherein the compensating function is an inverse transfer function matched to the filament response profile.

5. The x-ray beam control system, as in claim 1, wherein:
   the compensation circuit includes a controller that measures the filament response profile of the x-ray tube and derives the compensating function; and
   the controller generates the modified control signal according to the compensating function.

6. The x-ray beam control system, as in claim 5, the controller including memory storing values of the compensating function in a lookup table.

7. The x-ray beam control system, as in claim 5, wherein:
   the controller acquires first and second filament response profiles of the x-ray tube at different times;
   the controller further comprising a comparator receiving and comparing the first filament response profile and the second filament response profile, and generating filament health indicator.

8. The x-ray beam control system, as in claim 7, wherein:
   the modulation circuit applies a series of duty cycle signals to the x-ray tube; and
   the controller stores the first and the second filament response profiles.

9. An x-ray beam control system, as in claim 7, wherein the controller acquiring first and second filament response profiles of the x-ray tube is user initiated.

10. An x-ray beam control system, as in claim 7, wherein the controller acquiring a acquiring first and second current filament response profiles occurs at predetermined operating intervals.

11. The x-ray beam control system, as in claim 1, further including a mode setting is a selected from a group including high current filament and precision current mode filament.

12. A portable spectrometer for analyzing composition of a sample comprising:
   a handheld housing encasing,
      a circuit including
         a feedback control loop circuit, including a modulation circuit, generating a control signal,
         an x-ray tube, having a filament response profile of tube current versus filament temperature which is non-linear, producing a beam of penetrating radiation for illuminating a spot on at least a portion of the sample, thereby producing a response signal from the sample, and
         a compensation circuit receiving the control signal, modifying the control signal according to a compensating function that is matched to the filament response profile,
      wherein:
         the modulation circuit receives the modified control signal and generates a drive signal,
         the x-ray tube receives the drive signal at a filament thereof, and outputs a tube current signal having a linear response to the control signal; and
         the feedback control loop circuit receives the tube current signal;
      a detector receiving the response signal and producing an output signal; and
      a spectral analyzer receiving and analyzing the output signal.

13. The portable spectrometer, as in claim 12, further comprising a mode setting selected from a group including high current filament and precision current mode filament etc.

14. The portable spectrometer, as in claim 12, wherein the compensating function is an inverse transfer function matched to the non-linear response.

15. The portable spectrometer, as in claim 12, wherein:
the compensation circuit includes a controller that measures the filament response profile of the x-ray tube and derives the compensating function; and
the controller generates the modified control signal according to the compensating function.

16. The portable spectrometer, as in claim 15, the controller including memory storing values of the compensating transfer function in a lookup table.

17. The portable spectrometer, as in claim 12, further comprising a mode setting is a parameter selected from a group including high current filament and precision current mode filament;
wherein for each mode setting, there is a compensation function matching the filament response profile and the parameter.

18. The portable spectrometer, as in claim 12, further comprising:
the controller acquires first and second filament response profiles of the x-ray tube at different times;
the control system further comprising a comparator receiving and comparing the first filament response profile and the second filament response profile, and generating filament health indicator.

19. The portable spectrometer, as in claim 18, wherein:
the modulation circuit applies a series of duty cycle signals to the x-ray tube; and
the controller stores the first and the second filament response profiles.

20. The portable spectrometer, as in claim 18, wherein the controller acquiring a first and second filament response profiles of the x-ray tube is user initiated.

21. The portable spectrometer, as in claim 18, wherein the controller acquiring a acquiring first and second current filament response profiles occurs at predetermined operating intervals.

22. A method for controlling an x-ray beam control system comprising:
generating a control signal by a feedback control loop;
for an x ray tube, acquiring a filament response profile of tube current versus filament temperature which is non-linear; and
modifying the control signal according to a compensating function that is matched to the filament response profile;
generating a drive signal in response to the modified control signal;
receiving the drive signal at a filament of the x-ray tube;
the x-ray tube outputting a tube current having a linear response to the control signal; and
receiving the tube current signal by the feedback control loop.

23. The method for controlling an x-ray beam control system, as in claim 22, wherein the compensating function is an inverse transfer function matched to the filament response profile.

24. The method for controlling an x-ray beam control system, as in claim 22, acquiring a filament response profile of a tube current versus filament temperature comprising:
measuring the filament response profile of the x-ray tube; and
deriving the compensating function.

25. The method for controlling an x-ray beam control system, as in claim 22, comprising storing values of the compensating function in a lookup table.

26. The method for controlling an x-ray beam control system, as in claim 22, further comprising:
acquiring first and second filament response profiles of the x-ray tube at different times;
comparing the first filament response profile and the second filament response profile; and
generating filament health indicator.

27. The method for controlling an x-ray beam control system, as in claim 22, acquiring first and second filament response profiles at diffferent times comprising:
applying a series of duty cycle signals to the x-ray tube; and
storing the first and the second filament response profiles and compensating functions matched to the first and the second filament response profiles.

28. A non-transitory computer-readable storage medium embodying a program of machine-readable instruction, executable by a processor, to perform operations to control an x-ray beam control system, the operations comprising:
generating a control signal by a feedback control loop of the x-ray beam control system;
for an x ray tube of the x-ray beam control system, acquiring a filament response profile of tube current versus filament temperature which is non-linear; and
modifying the control signal according to a compensating function that is matched to the filament response profile;
generating a drive signal in response to the modified control signal;
receiving the drive signal at a filament of the x-ray tube;
the x-ray tube outputting a tube current having a linear response to the control signal; and
receiving the tube current signal by the feedback control loop.

* * * * *

UNITED STATES PATENT AND TRADEMARK OFFICE
CERTIFICATE OF CORRECTION

PATENT NO. : 8,964,940 B2  
APPLICATION NO. : 13/683376  
DATED : February 24, 2015  
INVENTOR(S) : David J. Caruso and Mark T. Dinsmore It is certified that error appears in the above-identified patent and that said Letters Patent is hereby corrected as shown below:

In the claims

Column 6, line 27, In Claim 10, delete "acquiring a acquiring" and insert -- acquiring a --, therefor.

Column 6, line 31, In Claim 11, delete "is a selected" and insert -- is selected --, therefor.

Column 7, line 34, In Claim 21, delete "acquiring a acquiring" and insert -- acquiring a --, therefor.

Column 8, line 25, In Claim 27, delete "diffferent" and insert -- different --, therefor.

Column 8, line 37, In Claim 28, delete "x ray" and insert -- x-ray --, therefor.

Signed and Sealed this  
Third Day of May, 2016

Michelle K. Lee  
*Director of the United States Patent and Trademark Office*